(12) United States Patent
Sato

(10) Patent No.: US 11,179,058 B2
(45) Date of Patent: Nov. 23, 2021

(54) MEDICAL PRODUCT EMITTING NEAR-INFRARED FLUORESCENCE AND MEDICAL PRODUCT USAGE STATUS CHECKING APPARATUS

(71) Applicants: National University Corporation Kochi University, Kochi (JP); DIC Corporation, Tokyo (JP)

(72) Inventor: Takayuki Sato, Kochi (JP)

(73) Assignees: NATIONAL UNIVERSITY CORPORATION KOCHI UNIVERSITY, Kochi (JP); DIC CORPORATION, Tokyo (JP)

(*) Notice: Subject to any disclaimer, the term of this patent is extended or adjusted under 35 U.S.C. 154(b) by 1106 days.

(21) Appl. No.: 14/404,707

(22) PCT Filed: May 28, 2013

(86) PCT No.: PCT/JP2013/064764
§ 371 (c)(1),
(2) Date: Dec. 1, 2014

(87) PCT Pub. No.: WO2013/180127
PCT Pub. Date: Dec. 5, 2013

(65) Prior Publication Data
US 2015/0148665 A1      May 28, 2015

(30) Foreign Application Priority Data

Jun. 1, 2012 (JP) .............................. JP2012-125710
Jun. 1, 2012 (JP) .............................. JP2012-125712

(51) Int. Cl.
A61B 5/00      (2006.01)
G01N 27/82     (2006.01)
(Continued)

(52) U.S. Cl.
CPC ............ *A61B 5/061* (2013.01); *A61B 5/0071* (2013.01); *A61B 17/06066* (2013.01); (Continued)

(58) Field of Classification Search
CPC . A61B 5/061; A61B 5/0071; A61B 17/06066; A61B 17/06166; A61M 39/0208; G01N 21/6486
See application file for complete search history.

(56) References Cited

U.S. PATENT DOCUMENTS

| | | |
|---|---|---|
| 5,667,840 A | 9/1997 | Tingey et al. |
| 5,807,605 A | 9/1998 | Tingey et al. |

(Continued)

FOREIGN PATENT DOCUMENTS

| | | |
|---|---|---|
| CA | 2197158 A1 | 8/1997 |
| CN | 102429629 A | 5/2012 |

(Continued)

OTHER PUBLICATIONS

International Preliminary Report on Patentability dated Dec. 4, 2014.
(Continued)

*Primary Examiner* — Patricia J Park
(74) *Attorney, Agent, or Firm* — Nixon Peabody LLP

(57) ABSTRACT

An apparatus to determine if a constituent member has been damaged. The constituent member can be a medical product comprising a coating, or a substance kneaded into the product, which emits a fluorescence in the near-infrared region. The apparatus to determine if this constituent member has been damaged includes an irradiation light source, an optical filter, an imaging unit, a display unit and a control unit connected to the light source, the optical filter and the imaging unit to determine and inform that damage has occurred in the constituent member.

4 Claims, 7 Drawing Sheets

(51) Int. Cl.
  *A61B 5/06*   (2006.01)
  *A61M 39/02*   (2006.01)
  *A61B 17/06*   (2006.01)
  *G01N 21/64*   (2006.01)
  *A61M 39/00*   (2006.01)
  *A61B 90/00*   (2016.01)
  *A61B 90/90*   (2016.01)

(52) U.S. Cl.
  CPC ... *A61B 17/06166* (2013.01); *A61M 39/0208* (2013.01); *G01N 21/6486* (2013.01); *A61B 90/90* (2016.02); *A61B 2090/0809* (2016.02); *A61B 2090/3941* (2016.02); *A61M 2039/0036* (2013.01); *A61M 2039/0238* (2013.01); *A61M 2039/0244* (2013.01); *A61M 2205/3313* (2013.01); *A61M 2205/6063* (2013.01); *G01N 2201/062* (2013.01)

(56) References Cited

U.S. PATENT DOCUMENTS

| | | | |
|---|---|---|---|
| 2005/0182318 A1 | 8/2005 | Kaji et al. | |
| 2010/0269837 A1* | 10/2010 | Levinson | A61B 5/145 128/899 |
| 2011/0017217 A1* | 1/2011 | Wood | A61M 16/04 128/207.14 |
| 2011/0077676 A1 | 3/2011 | Sivan et al. | |
| 2011/0092811 A1 | 4/2011 | Yasui | |
| 2011/0160577 A1 | 6/2011 | Kaji et al. | |
| 2011/0237942 A1 | 9/2011 | Zako et al. | |
| 2011/0275930 A1* | 11/2011 | Jho | A61B 5/064 600/424 |
| 2011/0311416 A1 | 12/2011 | Palmer et al. | |
| 2012/0059222 A1 | 3/2012 | Yoshida | |
| 2012/0082713 A1* | 4/2012 | Meyering | A61L 29/085 424/423 |
| 2013/0079467 A1* | 3/2013 | Bruns | C08K 9/08 525/54.1 |
| 2013/0253312 A1 | 9/2013 | Sato et al. | |

FOREIGN PATENT DOCUMENTS

| | | |
|---|---|---|
| EP | 793089 A2 | 9/1997 |
| EP | 1561420 A2 | 8/2005 |
| EP | 2275029 A2 | 1/2011 |
| JP | H09236554 A | 9/1997 |
| JP | 2005218680 A | 8/2005 |
| JP | 2006122321 A | 5/2006 |
| JP | 2006301523 A | 11/2006 |
| JP | 2008515586 A | 5/2008 |
| JP | 2012055351 A | 3/2012 |
| JP | 2012-115535 A | 6/2012 |
| WO | WO-2009154081 A1 | 12/2009 |

OTHER PUBLICATIONS

Written Opinion dated Jul. 9, 2013.
Supplementary Partial European Search Report dated May 23, 2016 from European Application No. 13796468.0, pp. 1-9.
International Search Report and Written Opinion dated Jul. 9, 2013.
International Preliminary Report on Patentability dated Jul. 8, 2014.
Written Opinion dated Apr. 28, 2014.

* cited by examiner

MEDICAL PRODUCT EMITTING NEAR-INFRARED FLUORESCENCE AND MEDICAL PRODUCT USAGE STATUS CHECKING APPARATUS

CROSS-REFERENCE TO RELATED APPLICATIONS

This application is a National Phase filing under 35 U.S.C. § 371 of PCT Patent Application Serial No. PCT/JP2013/064764 filed on May 28, 2013, which claims priority of Japanese Patent Application Serial No. 2012-125710 filed on Jun. 1, 2012, and Japanese Patent. Application Serial No. 2012-125712 filed on Jun. 1, 2012 the entire contents of all of which are hereby incorporated by reference in their entireties.

TECHNICAL FIELD

The present invention relates to a medical product emitting near-infrared fluorescence and a medical product usage status checking apparatus.

BACKGROUND ART

In a subcutaneous implanted port which is implanted beneath skin in order to inject a medicine in a blood vessel or in a sealed container which contains an infusion substance or the like, a septum into which an injection needle is injected is used as its constituent member. The septum is configured with a silicone rubber and is attached to a housing or the like of the port so as to receive a compression force in order to increase sealability. In some cases, when the injection needle punctures the septum, a portion of the septum may be scraped off due to a heel portion of the injection needle. The scraped separate piece is called a "core", and the phenomenon that the core is generated by the puncturing of the injection needle is called "coring". In order to prevent the core together with a medicine from entering a blood vessel, there is a demand to check the damage status such as coring as the usage status of the medical product.

In addition, in surgery, a lot of cloth-formed consumable items such as suture needles, suture threads and gauze and a lot of nonwoven cloth-formed consumable items such as absorbent cottons are used. In order to prevent these medical products from remaining in a living body, there is a demand to check whether or not the medical product exists in an operative field as the usage status of the medical product.

Patent Literature 1 discloses a technique of attaching a radio frequency identification (RFID) tag to a medical product, scanning the medical product to read information recorded in the RFID tag after surgery or the like, and checking a type, a position, or the like of the medical product.

A technique of performing coating with a fluorescent material for the purpose of displaying or improving visibility in a medical field is known (refer to Patent Literature 2). In addition, a technique of visualizing a blood vessel by applying a principle that near-infrared rays pass through skin and are absorbed by hemoglobin of red blood cells is known (refer to Patent Literature 3).

CITATION LIST

Patent Literatures

Patent Literature 1: JP-2006-122321 A
Patent Literature 2: JP-2008-515586 W
Patent Literature 3: WO 2009/154081 A

SUMMARY OF INVENTION

Technical Problem

However, the technique disclosed in Patent Literature 1 is to prevent an accident that the medical product remains by checking the current position of the medical product. Therefore, in the technique, it is not possible to check the damage of the medical product. In addition, the medical product as a target for checking the existence or nonexistence is limited to the medical product of which size is suitable for attachment of the RFID tag.

Like this, there is no disclosure of a technique capable of checking a damage status of a medical product as a usage status of the medical product in the case of using the medical product were a portion of the constituent member of the medical product is separated as a separate piece due to damage. In addition, there is no disclosure of a technique capable of checking existence or nonexistence of a medical product such as a suture needle or a suture thread which is too small to attach an RFID tag as a usage status of the medical product.

In addition, in the technique of Patent Literature 3, coating of implantation with a fluorescent material is performed in order to easily identify implantation. However, the fluorescence in use is fluorescence which can be visually identified, that is, visible light fluorescence. In Patent Literature 3, a technique using near-infrared fluorescence is not disclosed.

In a technique of Patent Literature 4, a blood vessel is visualized by a near-infrared camera including a near-infrared light source in order to output a positional relationship between a needle of an injection needle as a medical product and the blood vessel as a plane image to a monitor. However, since it is presumed that a shape of the injection needle in use is specified in advance, the technique is only to estimate a position of a distal end of the injection needle which is inserted into a subcutaneous portion. In Patent Literature 4, a technique of visualizing an injection needle which is inserted into a subcutaneous portion is not disclosed.

The present invention is to provide a medical product emitting near-infrared fluorescence and a medical product usage status checking apparatus capable of accurately checking a usage status of a medical product such as a damage status of the medical product in the case of using the medical product where a portion of a constituent member is separated as a separate piece due to damage or existence or nonexistence of the medical product such as a suture needle or a suture thread which is relatively small.

Means for Solving Problem

According to the present invention for achieving the above object, there is provided a medical product emitting near-infrared fluorescence which is configured to include at least one light-emissive constituent member which includes a luminescent agent emitting near-infrared fluorescence according to irradiation of excitation light on a surface thereof. Even in a case where a portion of a constituent member is separated as a separate piece from the constituent member due to damage, the luminescent agent is also included on a surface of the separate piece.

In addition, according to the present invention, there is provided a light-emissive medical product which includes a luminescent agent emitting near-infrared fluorescence according to irradiation of excitation light on a surface thereof, wherein the medical product emitting near-infrared fluorescence is a light-emissive suture needle where the luminescent agent is applied on a surface thereof, a light-emissive suture thread which is formed with a synthetic thread where the luminescent agent is kneaded in a resin material, a light-emissive cloth-formed consumable item into which the synthetic thread is woven, or a light-emissive nonwoven cloth-formed consumable item which includes the synthetic thread without weaving.

According to the present invention for achieving the above object, there is provided a medical product usage status checking apparatus including: a medical product including at least one light-emissive constituent member which includes a luminescent agent emitting near-infrared fluorescence according to irradiation of excitation light on a surface thereof, wherein even in a case where a portion of the constituent member is separated as a separate piece from the constituent member due to damage, the luminescent agent is also included on a surface of the separate piece; an irradiation unit which includes a light source emitting excitation light which excites the luminescent agent and irradiates the medical product with the excitation light emitted from the light source; an optical filter which blocks the excitation light and transmits the near-infrared fluorescence emitted by the luminescent agent; an imaging unit which receives the near-infrared fluorescence passing through the optical filter; and a display unit which displays an image captured by the imaging unit. An image based on the near-infrared fluorescence of the constituent member is displayed on the display unit, and in a case where damage occurs in the constituent member, an image based on the near-infrared fluorescence of the separate piece is displayed on the display unit.

In addition, according to the present invention, there is provided a medical product usage status checking apparatus including a light-emissive medical product which includes a luminescent agent emitting near-infrared fluorescence according to irradiation of excitation light on a surface thereof; an irradiation unit which includes alight source emitting excitation light which excites the luminescent agent and irradiates an operative field where existence or nonexistence of the medical product is to be checked with the excitation light emitted from the light source; an optical filter which blocks the excitation light and transmits the near-infrared fluorescence emitted by the luminescent agent; an imaging unit which receives the near-infrared fluorescence passing through the optical filter; and a display unit which displays an image captured by the imaging unit. In a case where the medical product exists in the operative field, an image based on the near-infrared fluorescence of the medical product is displayed on the display unit.

Advantageous Effect of the Invention

The medical product emitting near-infrared fluorescence is configured to include at least one light-emissive constituent member which includes a luminescent agent emitting near-infrared fluorescence according to irradiation of excitation light on a surface thereof. In addition, even in a case where a portion of a constituent member is separated as a separate piece from the constituent member due to damage, the luminescent agent is also included on a surface of the separate piece. Therefore, by applying the medical product usage status checking apparatus, it is possible to accurately and easily check a position of the constituent member in the medical product. In addition, it is possible to accurately and easily check the occurrence of damage in the constituent member and the damage status, so that it is possible to perform appropriate measures according to the usage status of the medical product.

The medical product emitting near-infrared fluorescence is a light-emissive suture needle, a light-emissive suture thread, a light-emissive cloth-formed consumable item, or a light-emissive nonwoven cloth-formed consumable item which includes a luminescent agent emitting near-infrared fluorescence according to irradiation of excitation light on a surface thereof. Therefore, by applying the medical product usage status checking apparatus, it is possible to check the existence or nonexistence of the medical product. When an image based on the near-infrared fluorescence appears on the display unit, a user can accurately and easily check the existence of the medical product in the operative field and the position where the medical product exists, so that it is possible to perform appropriate measures according to the usage status of the medical product such as removal of the medical product.

According to the medical product usage status checking apparatus, an image based on the near-infrared fluorescence of the constituent member is displayed on the display unit, and in a case where damage occurs in the constituent member, an image based on the near-infrared fluorescence of the separate piece is displayed on the display unit. Therefore, it is possible to accurately and easily check the position of the constituent member in the medical product. In addition, it is possible to accurately and easily check the occurrence of damage in the constituent member or the damage status, so that it is possible to perform appropriate measures according to the usage status of the medical product.

According to the medical product usage status checking apparatus, in a case where the medical product exists in the operative field, an image based on the near-infrared fluorescence of the medical product is displayed on the display unit. Therefore, it is possible to accurately and easily check the existence of the medical product in the operative field and the position where the medical product exists, so that it is possible to perform appropriate measures according to the usage status of the medical product such as removal of the medical product. In addition, since the existence or nonexistence is checked based on the near-infrared fluorescence, the present invention is not limited by the size of the medical product which is a target for checking the existence or nonexistence.

BRIEF DESCRIPTION OF DRAWINGS

FIG. 6(A) illustrates a case where excitation light is off, and FIG. 6(B) illustrates a case where excitation light is on.

FIG. 7(A) illustrates a case where excitation light is off, and FIG. 7(B) illustrates a case where excitation light is on.

DESCRIPTION OF EMBODIMENTS

Figure 1:
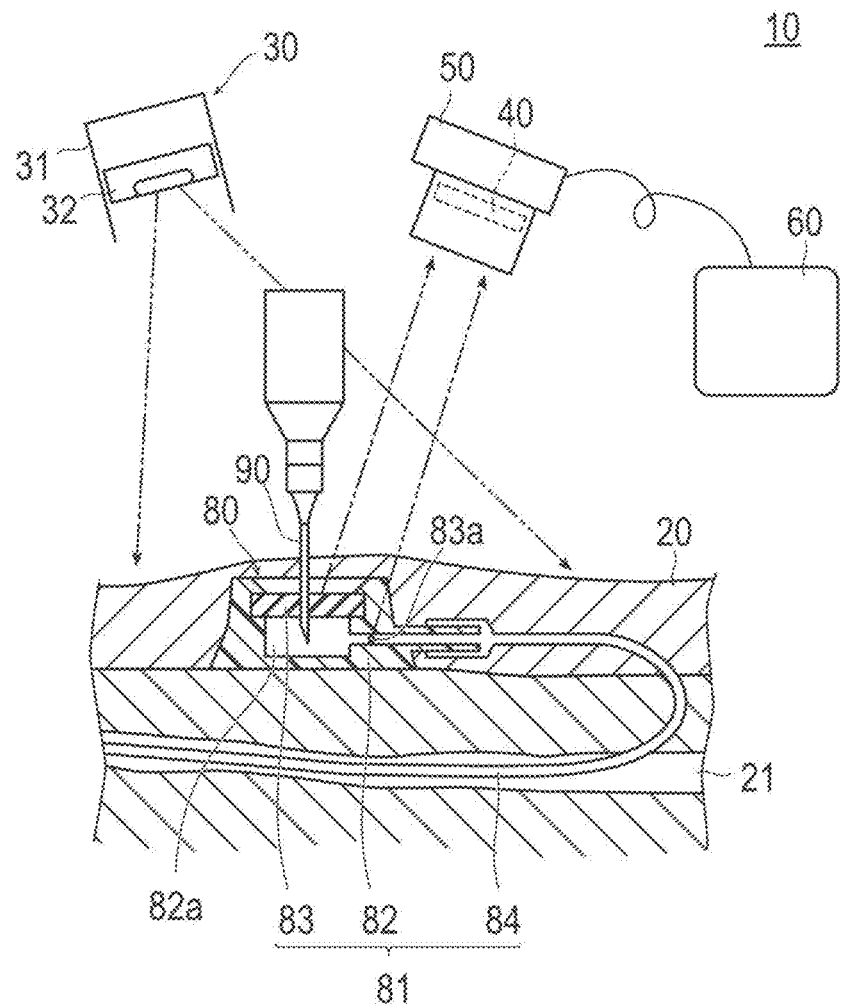
FIG. 1 is an explanatory drawing illustrating a medical product usage status checking apparatus according to a first embodiment.

Hereinafter, embodiments of the present invention will be described with reference to the attached drawings. In addition, in the description of the drawings, the same components are denoted by the same reference numerals, and the redundant description is not presented. In the drawings, dimension ratios are exaggerated for the convenience of description and are different from actual ratios.

First Embodiment

Figure 2:
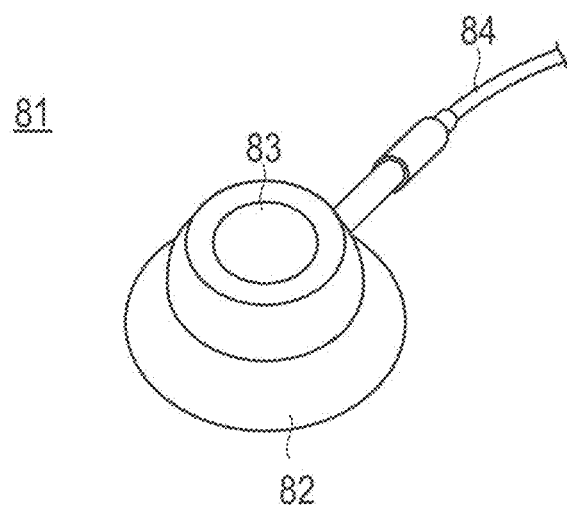
FIG. 2 is a perspective view illustrating a subcutaneous implanted port illustrated in FIG. 1.

FIG. 1 is an explanatory drawing illustrating a medical product usage status checking apparatus 10 according to a first embodiment, and FIG. 2 is a perspective view illustrating a subcutaneous implanted port 81 illustrated in FIG. 1.

Referring to FIG. 1, a medical product 80 emitting near-infrared fluorescence which is a target for checking usage status thereof is configured to include at least one light-emissive constituent member 83 which includes a luminescent agent emitting near-infrared fluorescence according to irradiation of excitation light on a surface thereof. Therefore, even in a case where a portion of the constituent member 83 is separated as a separate piece 83a from the constituent member 83 due to damage, the luminescent agent is included also on a surface of the separate piece 83a. As described in brief, the medical product usage status checking apparatus 10 according to the first embodiment is configured to include the medical product 80 emitting near-infrared fluorescence, an irradiation unit 30 which includes a light source 32 emitting excitation light which excites the luminescent agent and irradiates the medical product 80 with the excitation light emitted from the light source 32, an optical filter 40 which blocks the excitation light and transmits the near-infrared fluorescence emitted by the luminescent agent, a camera 50 (corresponding to an imaging unit) which receives the near-infrared fluorescence passing through the optical filter 40, and a monitor 60 (corresponding to a display unit) which displays an image captured by the camera 50. In the medical product usage status checking apparatus 10, an image based on the near-infrared fluorescence of the constituent member 83 is displayed on the monitor 60, and in a case where damage occurs in the constituent member 83, an image based on the near-infrared fluorescence of the separate piece 83a is displayed on the monitor 60. Hereinafter, the description will be made in detail.

The medical product 80 illustrated in FIG. 1 is a subcutaneous implanted port 81 which is implanted beneath skin 20 in order to inject a medicine in a blood vessel. The subcutaneous implanted port 81 is used for a patient or the like who is repetitively subjected to drip infusion or the like. As illustrated in FIG. 2, the subcutaneous implanted port 81 is configured to include a housing 82 constituting an injection chamber 82a, a septum 83 mounted on an upper portion of the housing 82, and a catheter 84 attached to the housing 82. The one end of the catheter 84 communicates with the injection chamber 82a, and the other end is inserted into a blood vessel 21. The septum 83 is mounted to the housing 82 so as to receive a compression force to enhance sealability. An injection needle 90 such as a Huber needle is inserted into the septum 83.

In a case where the injection needle 90 punctures in the state where the injection needle is inclined with respect to an upper surface of the septum 83, there is a concern that a portion of the septum 83 is scraped off by a heel portion of the injection needle 90, so that a core 83a as a separate piece is generated. In the subcutaneous implanted port 81, the light-emissive constituent member is at least the septum 83. This is because it is possible to check a damage status such as coring as a usage status of the medical product 80 in order to prevent the core 83a together with a medicine from entering the blood vessel 21. Furthermore, this is because it is possible to accurately check a site where the subcutaneous implanted port 81 is implanted or a to-be-punctured position by allowing the septum 83 to emit the near-infrared fluorescence. In addition to the septum 83, the housing 82 may be allowed to be light-emissive, or a portion of or all the portions of the catheter 84 may be allowed to be light-emissive.

The septum 83 as a constituent member is configured so that a luminescent agent is applied on a surface thereof or is configured with a material in which a luminescent agent is kneaded. It is possible to allow the septum 83 itself to emit light, and in a case where a portion of the septum 83 is damaged and the core 83a is generated, the luminescent agent is included on the surface of the core 83a, so that it is also possible to allow the core 83a to emit light. In the illustrated example, the septum 83 is configured with a silicone rubber in which a luminescent agent is kneaded.

The luminescent agent is a medicine which can be used for a human body or an animal. If a material emits the near-infrared fluorescence according to irradiation of the excitation light, the appropriate material may be used. Herein, the excitation wavelength is in a wavelength range suitable for allowing the luminescent agent to emit light. The excitation wavelength is preferably in a wavelength range of near-infrared light, and the light having a wavelength range of 600 nm to 1400 nm may be used. The near-infrared light has high transmittance with respect to human tissues such as skin, fat, and muscle and is capable of being transmitted down to about 5 mm to 20 mm under the surface of the tissue of the living body. Therefore, even in the case of the subcutaneous implanted port 81 used in the state where it is implanted in the living body, by allowing the excitation light to be transmitted down to the position where the septum 83 is implanted, the septum 83 and the core 83a which is generated due to the damage can be allowed to emit light.

More specifically, as the luminescent agent, indocyanine green (ICG) or an azo-boron complex compound disclosed in Japanese Patent Application No. 2010-23479 (JP 2011-162445 A) filed by the inventors of the present invention which emits near-infrared fluorescence according to irradiation of the excitation light may be used. The indocyanine green is a colorant which absorbs near-infrared excitation light having a wavelength range of about 800 nm to be excited and emits near-infrared fluorescence having a wavelength of about 850 nm. The azo-boron complex compound is a compound where a hydrazone compound is subjected to boron complexation to improve light absorption characteristics and light emission characteristics so as to emit strong near-infrared fluorescence. The azo-boron complex compound is easy to disperse in a polymer resin, and similarly to the case of the compound alone, even in the case of manufacturing a fluorescent film by dispersing the compound in a resin, excellent light absorption characteristics and excellent light emission characteristics can be obtained. As an example of the light absorption characteristics and the light emission characteristics of the azo-boron complex compound, in the case of the compound alone, the maximum absorption wavelength is 674 nm and the maximum fluorescence wavelength is 743 nm (refer to Example 1 (2) of Table 1 of Publication Document), and in the case of manufacturing the fluorescent film, the maximum absorption wavelength is 662 nm and the maximum fluorescence wavelength is 702 nm (refer to Example 1 (2) of Table 2 of Publication Document).

The irradiation unit 30 is configured to include a chassis 31 and a light source 32 which is arranged in the chassis 31 to emit excitation light which excites the luminescent agent. The chassis 31 is configured with a metal material such as aluminum which does not transmit the excitation light. The subcutaneous implanted port 81 which is implanted in a living body is irradiated with the excitation light emitted from the light source 32. As the light source 32, for example, an LED or the like which emits the near-infrared excitation light having a wavelength range of 600 nm to 1400 urn may be used.

The optical filter 40 may be inserted between an imaging element and a lens in the camera 50 or may be arranged in front of the camera 50. The optical filter 40 is preferably set so that the transmittance of visible light is lower than that of the near-infrared fluorescence. This is because a weak near-infrared fluorescence image can be clearly displayed on a visible light image.

As the camera 50, a near-infrared CCD camera, a near-infrared CMOS camera, or the like which captures the near-infrared fluorescence passing through the optical filter 40 is used. The CCD camera is a camera configured with a charge coupled device element, and the CMOS camera is a camera using a complementary metal oxide semiconductor. The data acquired by the near-infrared CCD camera or the like are subjected to image processes such as a noise process, an edge process, and contrast enhancement and image analysis to be converted into data for images which are to be displayed on the monitor 60.

The camera 50 can image the entire septum 83 by receiving the near-infrared fluorescence emitted by the luminescent agent of the septum 83 by using a light-receiving element. The near-infrared fluorescence emitted by the luminescent agent of the septum 83 passes through a living tissue, and the camera 50 images the septum 83 by receiving the near-infrared fluorescence. In addition, at the same time, the camera 50 images the outline or the like of the human body.

In addition, the image captured by the camera 50 may be a monochrome image or may be a color image. The camera 50 may be configured so that the light source 32 is arranged in a ring shape around the lens. Accordingly, it is possible to more appropriately image the medical product 80.

If the monitor 60 can display an image captured by the camera 50, the monitor is not particularly limited. The monitor may be a table-top display or may be a head-mounted display. The displayed image may be any one of a monochrome image and a color image. On the monitor 60, an image based on the near-infrared fluorescence of the septum 83 is displayed, and in a case where damage occurs in the septum 83, an image based on the near-infrared fluorescence of the core 83a is displayed. A user views the image displayed on the monitor 60 to check the position of the septum 83 in the subcutaneous implanted port 81, the occurrence of damage in the septum 83, or the damage status.

Next, functions of the embodiment will be described.

As illustrated in FIG. 1, the subcutaneous implanted port 81 including the light-emissive septum 83 is implanted in the body of a patient in advance.

When the medicine is injected into the blood vessel 21 through the subcutaneous implanted port 81, the subcutaneous implanted port 81 is irradiated with the near-infrared excitation light emitted from the light source 32 by the irradiation unit 30. If the near-infrared excitation light passes through the living body to irradiate the septum 83, the septum 83 emits the near-infrared fluorescence. In the case of using indocyanine green as the luminescent agent, the luminescent agent absorbs the near-infrared excitation light having a wavelength range of about 800 nm to be excited and emits the near-infrared fluorescence having a wavelength of about 850 nm.

The near-infrared fluorescence emitted by the septum 83 passes through the optical filter 40 and is received by the camera 50, and thus, the image based on the near-infrared fluorescence of the septum 83 is displayed on the monitor 60. In addition, reflection light reflected on a surface of the living body is also received by the camera 50, so that an image of the outline of the living body together with the image of the septum 83 is also displayed on the monitor 60. The user views the image displayed on the monitor 60, so that the user can accurately and easily check the position of the septum 83 in the subcutaneous implanted port 81. Since the position of the septum 83 is the position where the injection needle 90 is to puncture, the user can accurately and easily check the punctured position.

In a case where the injection needle 90 is inserted to the septum 83, the subcutaneous implanted port 81 is also irradiated with the near-infrared excitation light.

In some cases, a portion of the septum 83 is scraped off by a heel portion of the injection needle 90, so that the core 83a is generated. Since the luminescent agent is included on the surface of the core 83a, in a case where coring occurs, if the core 83a is irradiated with the near-infrared excitation light, the core 83a emits the near-infrared fluorescence.

The near-infrared fluorescence emitted by the core 83a passes through the optical filter 40 and is received by the camera 50, and thus, the image based on the near-infrared fluorescence of the core 83a is displayed on the monitor 60. The user views the image displayed on the monitor 60, so that the user can accurately and easily check the occurrence of damage in the septum 83 or the damage status. By stopping injection of the medicine according to the usage status of the septum 83, it is possible to prevent the core 83a together with the medicine from entering the blood vessel 21 in advance.

In the medical product usage status checking apparatus 10, since X-ray is not used to check the usage status of the medical product 80, the problem in that operators and patients are exposed to the X-ray does not occur fundamentally. Furthermore, even in the case of the medical product 80 made from a resin or a rubber which transmits the X-ray, it is possible to check the usage status of the medical product.

As described above, in the first embodiment, the subcutaneous implanted port 81 emitting the near-infrared fluorescence is configured to include the light-emissive septum 83 which includes the luminescent agent emitting the near-infrared fluorescence according to irradiation of the excitation light on the surface thereof. In addition, even in a case where a portion of the septum 83 is separated as a core 83a from the septum 83 due to damage, the luminescent agent is also included on a surface of the core 83a. Therefore, by applying the medical product usage status checking apparatus 10 according to the embodiment, it is possible to accurately and easily check the position of the septum 83 in the subcutaneous implanted port 81, that is, the punctured position. Furthermore, it is possible to accurately and easily check the occurrence of damage in the septum 83 or the damage status, so that it is possible to perform appropriate measures according to the usage status of the medical product 80.

Since the septum 83 is configured so that the luminescent agent is applied on the surface thereof or is configured with a material in which the luminescent agent is kneaded, it is possible to allow the septum 83 itself to emit light, and in a case where a portion of the septum 83 is damaged and the core 83a is generated, the luminescent agent is included on the surface of the core 83a, so that it is also possible to allow the core 83a to emit light according to irradiation of the excitation light.

In the medical product usage status checking apparatus 10 according to the first embodiment, the image based on the near-infrared fluorescence of the septum 83 is displayed on the monitor 60, and in a case where damage occurs in the septum 83, the image based on the near-infrared fluorescence of the core 83a is displayed on the monitor 60. Therefore, it is possible to accurately and easily check the position of the septum 83 in the subcutaneous implanted port 81, that is, the punctured position. Furthermore, it is possible to accurately and easily check the occurrence of damage in the septum 83 or the damage status, so that it is possible to perform appropriate measures according to the usage status of the medical product 80.

Second Embodiment

Figure 3:
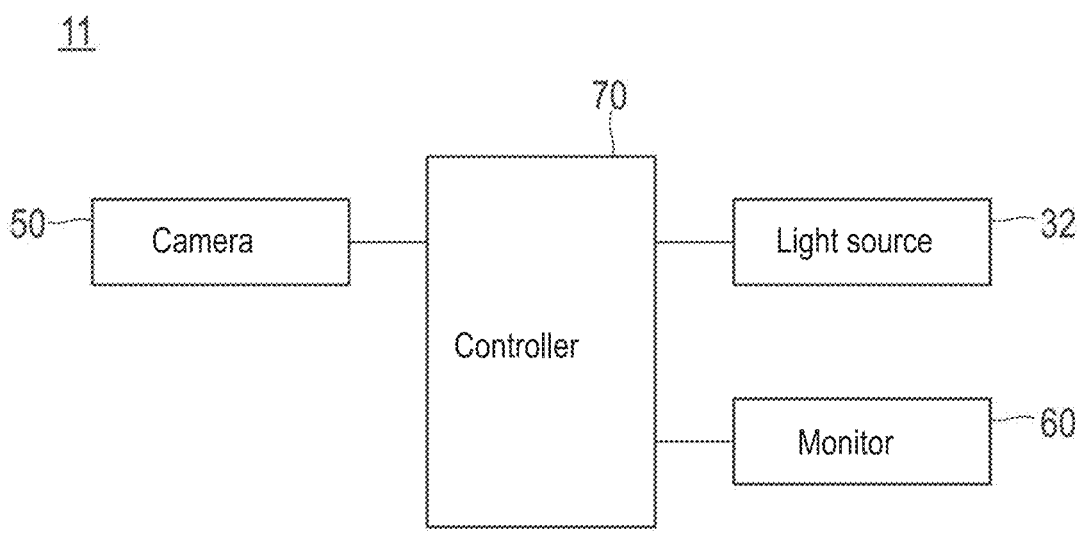
FIG. 3 is a schematic block diagram illustrating a configuration of a medical product usage status checking apparatus according to a second embodiment.

FIG. 3 is a schematic block diagram illustrating a configuration of a medical product usage status checking apparatus 11 according to a second embodiment. The same components as the first embodiment are denoted by the same reference numerals, and the description thereof is not partially presented.

Similarly to the first embodiment, the medical product usage status checking apparatus 11 according to the second embodiment is configured to include a subcutaneous implanted port 81 which emits near-infrared fluorescence, an irradiation unit 30, an optical filter 40, a camera 50, and a monitor 60. An image based on the near-infrared fluorescence of a septum 83 is displayed on the monitor 60, and in a case where damage occurs in the septum 83, an image based on the near-infrared fluorescence of a core 83a is displayed on the monitor 60.

In addition, in the second embodiment, the medical product usage status checking apparatus 11 includes a controller 70 (corresponding to a control unit) which informs that damage occurs in the septum 83 in a case where a first light-emitting region and a second light-emitting region of which the area is smaller than that of the first light-emitting region are detected from the image based on the near-infrared fluorescence.

The size of the core 83a which is generated due to the coring is much smaller than that of the septum 83. For this reason, the area of the image based on the near-infrared fluorescence of the core 83a is much smaller than that of the image based on the near-infrared fluorescence of the septum 83. Therefore, in a case where the first light-emitting region and the second light-emitting region of which the area is smaller than that of the first light-emitting region exist in the image based on the near-infrared fluorescence, it may be determined that the core 83a is generated due to the coring. The first light-emitting region is the region based on the near-infrared fluorescence of the septum 83, and the second light-emitting region is the region based on the near-infrared fluorescence of the core 83a.

The controller 70 performs image processes and image analysis on image data based on the near-infrared fluorescence to extract light-emitting regions, and in a case where a plurality of the light-emitting regions are detected, the controller calculates areas of the respective light-emitting regions. The controller 70 specifies the light-emitting region having a larger area as a first light-emitting region and specifies the light-emitting region having a smaller area as a second light-emitting region. When the area of the second light-emitting region to the area of the first light-emitting region is equal to or lower than a predetermined threshold value (for example, several %), the controller 70 determines that damage occurs in the septum 83. Therefore, the controller 70 informs a user that damage occurs in the septum 83. The informing is performed by displaying on the monitor 60 or generating warning sound.

In the medical product usage status checking apparatus 11 according to the second embodiment, since the medical product usage status checking apparatus further includes the controller 70 which informs that damage occurs in the septum 83 in a case where the first light-emitting region and the second light-emitting region of which the area is smaller than that of the first light-emitting region are detected from the image based on the near-infrared fluorescence, in addition to the functions and effects of the first embodiment, it is possible to more accurately and easily check the occurrence of damage in the septum 83 or the damage status, so that it is possible to more speedily perform appropriate measures according to the usage statue of the medical product 80.

(Modified Example of Medical Product 80)

Although the septum 83 of the subcutaneous implanted port 81 which is configured to be allowed to emit light as the medical product 80 emitting the near-infrared fluorescence is described in the first and second embodiments, the present invention is not limited to this case. The present invention may be applied to, for example, the medical products 80 illustrated in FIGS. 4 and 5.

Figure 4:
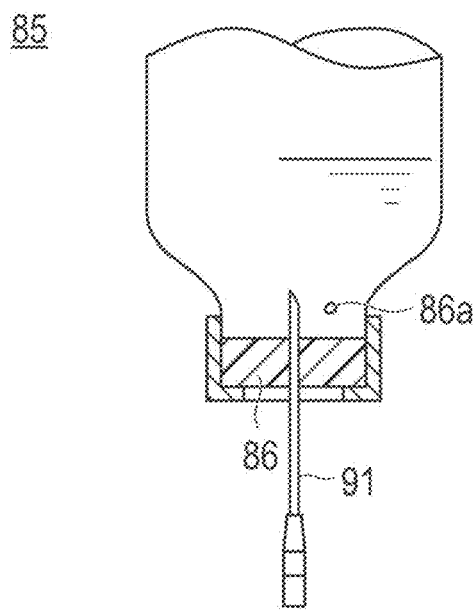
FIG. 4 is a perspective view illustrating a sealed container as a medical product.

The medical product 80 illustrated in FIG. 4 is a sealed container 85 in which an infusion substance or the like is contained. The sealed container 85 also includes a septum 86 into which an injection needle 91 is inserted as its constituent member. In the septum 86, the coring may also occur. Therefore, preferably, the septum 86 of the sealed container 85 is also configured so that a luminescent agent is applied on a surface thereof or is configured with a material in which a luminescent agent is kneaded. This is because, in a case where a portion of the septum 86 is damaged and the core 86a is generated, the luminescent agent is included on the surface of the core 86a, so that the core 86a can be allowed to emit light.

Therefore, by applying the above-described medical product usage status checking apparatuses 10 and 11, it is possible to accurately and easily check the occurrence of damage in the septum 86 of the sealed container 85 or the damage status, so that it is possible to perform appropriate measures according to the usage status of the medical product 80. Particularly, if the septum 86 and the infusion substance are similar in color or if the infusion substance is not transparent, since it is difficult to visually check the care 86a, the medical product usage status checking apparatuses 10 and 11 are usefully applied.

Figure 5:
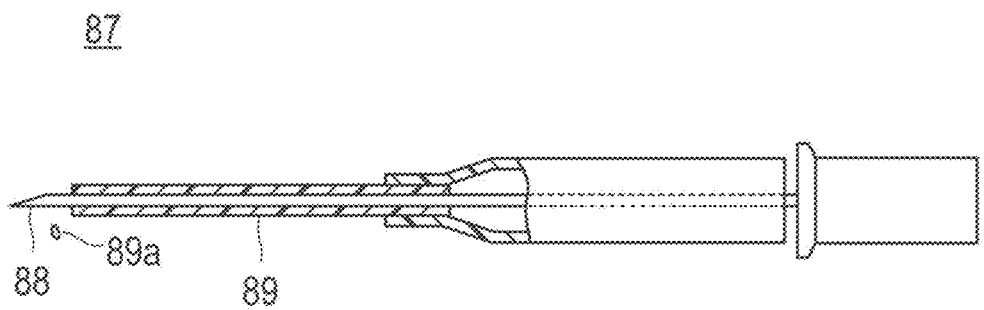
FIG. 5 is a partial cross-sectional view illustrating an indwelling needle as a medical product.

The medical product 80 illustrated in FIG. 5 is an indwelling needle 87 which indwells a needle tip in a blood vessel and is used, for example, in the case of performing external circulation in artificial dialysis, the case of performing transfusion in the blood vessel through drip infusion, or the like. The indwelling needle 87 is configured to include a hard inner needle 88 and a soft outer needle 89 into which the inner needle 88 is inserted. Although the puncture is performed by allowing the distal end of the inner needle 88 to protrude from the distal end of the outer needle 89, in some cases, a portion of the soft outer needle 89 may be scraped off by the distal end of the inner needle 88. In order to prevent the scraped separate piece 89a together with the medicine from entering the blood vessel, it is necessary to check the usage status of the soft outer needle 89 of the indwelling needle 87.

Therefore, in the indwelling needle 87, the soft outer needle 89 as its constituent member is configured to be allowed to emit light. The soft outer needle 89 includes a luminescent agent emitting near-infrared fluorescence according to irradiation of excitation light on a surface thereof. The surface including the luminescent agent is preferably both of an inner surface on which the hard inner needle 88 slides and an outer surface thereof. Even in a case where a portion of the outer needle 89 is separated as a separate piece 89a from the outer needle 89 due to damage, the luminescent agent is also included on a surface of the separate piece 89a. Preferably, the outer needle 89 is configured so that the luminescent agent is applied on the surface thereof or is configured with a material in which the luminescent agent is kneaded. This is because, in a, case where a portion of the outer needle 89 is damaged and the separate piece 89a is generated, the luminescent agent is included on the surface of the separate piece 89a, so that the separate piece 89a is allowed to emit light.

Therefore, similarly to the case of the septum 83 of the subcutaneous implanted port 81, by applying the above-described medical product usage status checking apparatuses 10 and 11, it is possible to accurately and easily check the occurrence of damage in the soft outer needle 89 of the indwelling needle 87 which punctures the blood vessel or the damage status, so that it is possible to perform appropriate measures according to the usage status of the medical product 80.

In addition, the present invention is not limited to the above-described medical products 90 (81, 85, and 87), but the present invention may be widely applied to a medical product 80 which has a risk of damage and of which usage status is desired to be checked. The medical product 80 is configured to include at least one light-emissive constituent member which includes a luminescent agent emitting near-infrared fluorescence according to irradiation of excitation light on a surface thereof, so that even in a case where a portion of the constituent member is separated as a separate piece from the constituent member due to damage, the luminescent agent may be included on a surface of the separate piece.

(Example of Observation of Emitting Status of Near-Infrared Fluorescence)

Figure 6:
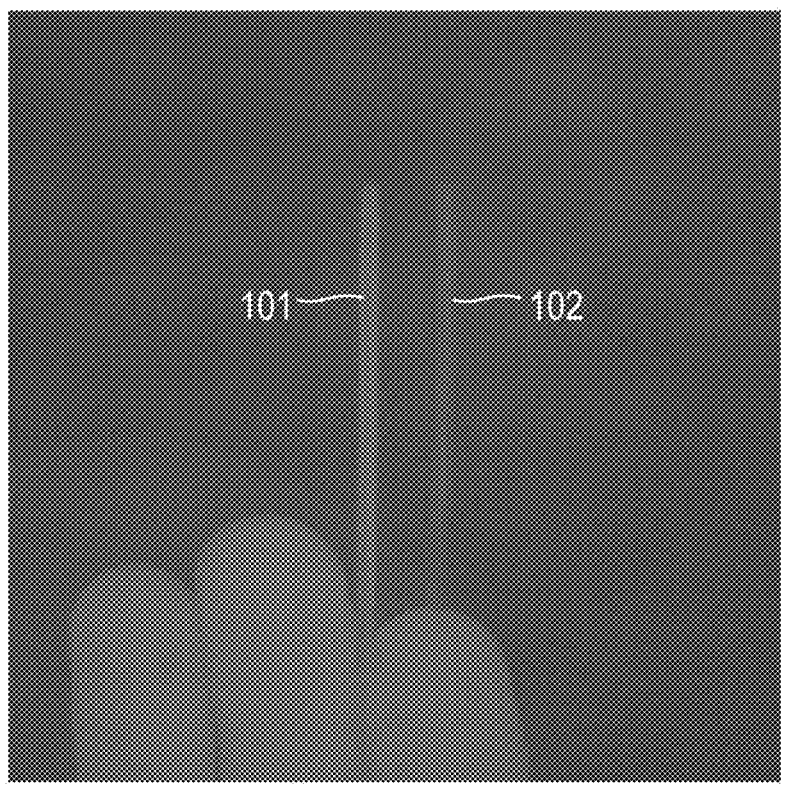
FIGS. 6(A) and 6(B) are images illustrating a status where a medical product emits near-infrared fluorescence in a case where the medical product is not implanted beneath skin.
Figure 6:
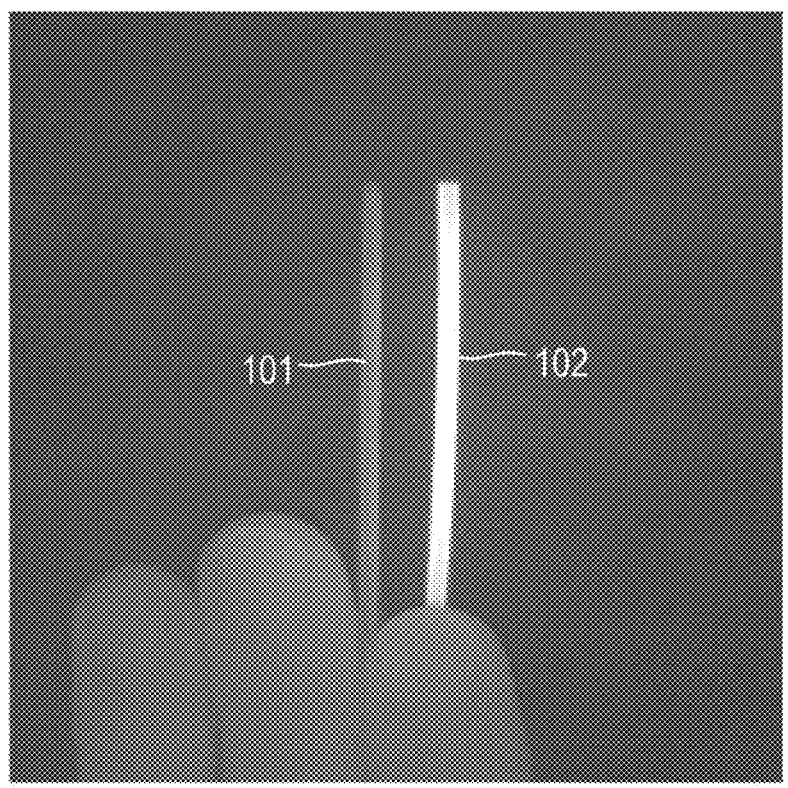

A status where a medical product emits near-infrared fluorescence according to irradiation of excitation light will be described. FIGS. 6(A) and 6(B) are images illustrating a status where a medical product emits near-infrared fluorescence in a case where medical product is not implanted beneath skin, FIG. 6(A) illustrates a case where excitation light is off, and FIG. 6(B) illustrates a case where excitation light is on. In addition, FIGS. 7(A) and 7(B) are images illustrating a status where a medical product emits near-infrared fluorescence in a case where the medical product is implanted beneath skin, FIG. 7(A) illustrates a case where excitation light is off, and FIG. 7(B) illustrates a case where excitation light is on.

In each of FIGS. 6(A) and 6(B), among two tubes 101 and 102, the tube 101 in the left side of the figures is a soft outer needle as a constituent member of a generally-used intravenous indwelling needle. The tube 102 in the right side of the figures is a light-emissive near-infrared fluorescent tube which includes a luminescent agent emitting the near-infrared fluorescence according to irradiation of the excitation light on a surface thereof. As the luminescent agent, an azo-boron complex compound of Example 1 of the above-described publication document (JP 2011-162445 A) was used.

As clearly seen from comparison of FIGS. 6(A) and 6(B), the near-infrared fluorescent tube 102 in the right side of the figures emitted the near-infrared fluorescence according to irradiation of the excitation light, so that the image based on the near-infrared fluorescence was clearly displayed on the monitor.

Figure 7:
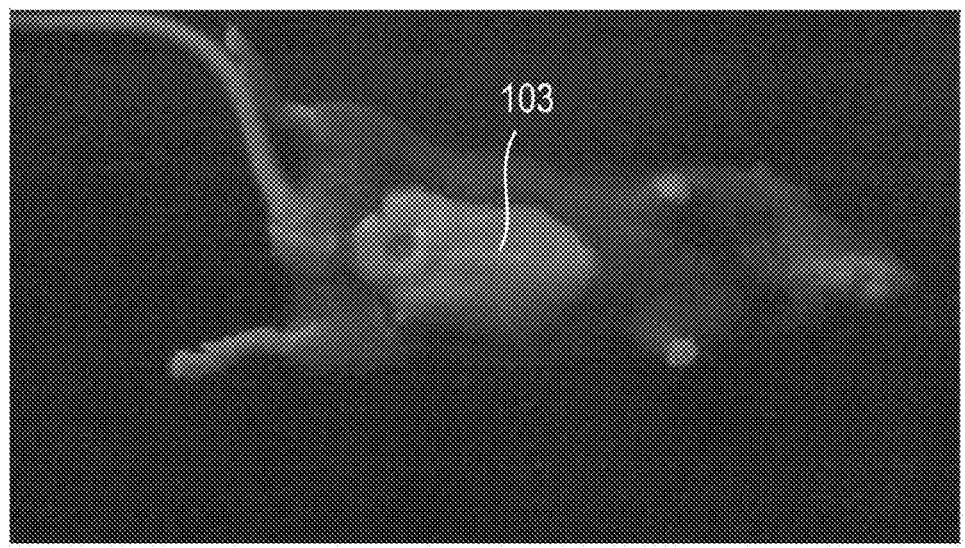
FIGS. 7(A) and 7(B) are images illustrating a status where a medical product emits near-infrared fluorescence in a case where the medical product is implanted beneath skin.
Figure 7:
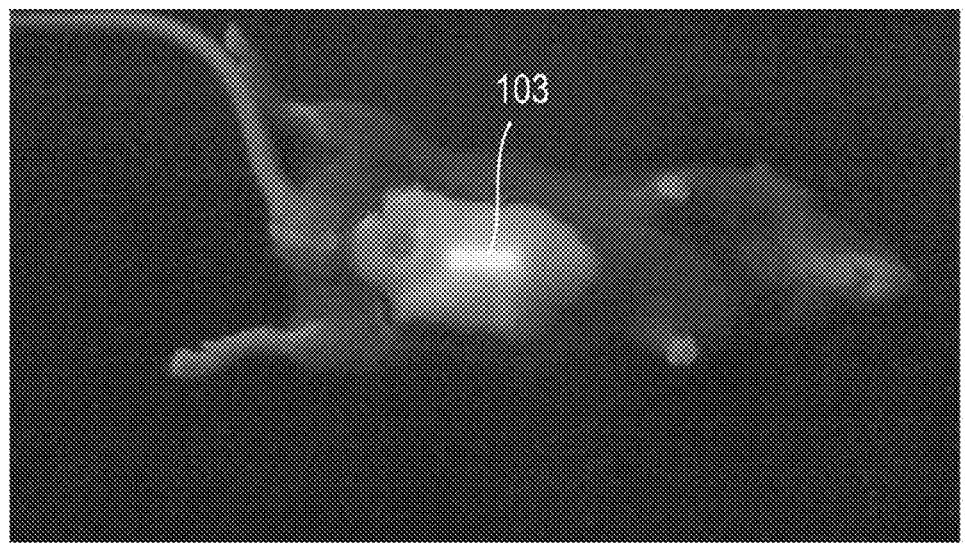

FIGS. 7(A) and 7(B) illustrate examples assuming a case where a constituent member of a medical product is damaged beneath skin. A piece 103 of the above-described near-infrared fluorescent tube 102 was implanted beneath skin of a mouse. As clearly seen from comparison of FIGS. 7(A) and 7(B), the piece 103 of the near-infrared fluorescent tube 102 existing beneath skin emitted the near-infrared fluorescence according to irradiation of the excitation light, so that the image based on the near-infrared fluorescence of the piece 103 was clearly displayed on the monitor. Therefore, it can be understood that it is possible to easily check the damage status of the constituent member of the medical product transdermally as the usage status of the medical product.

Third Embodiment

Figure 8:
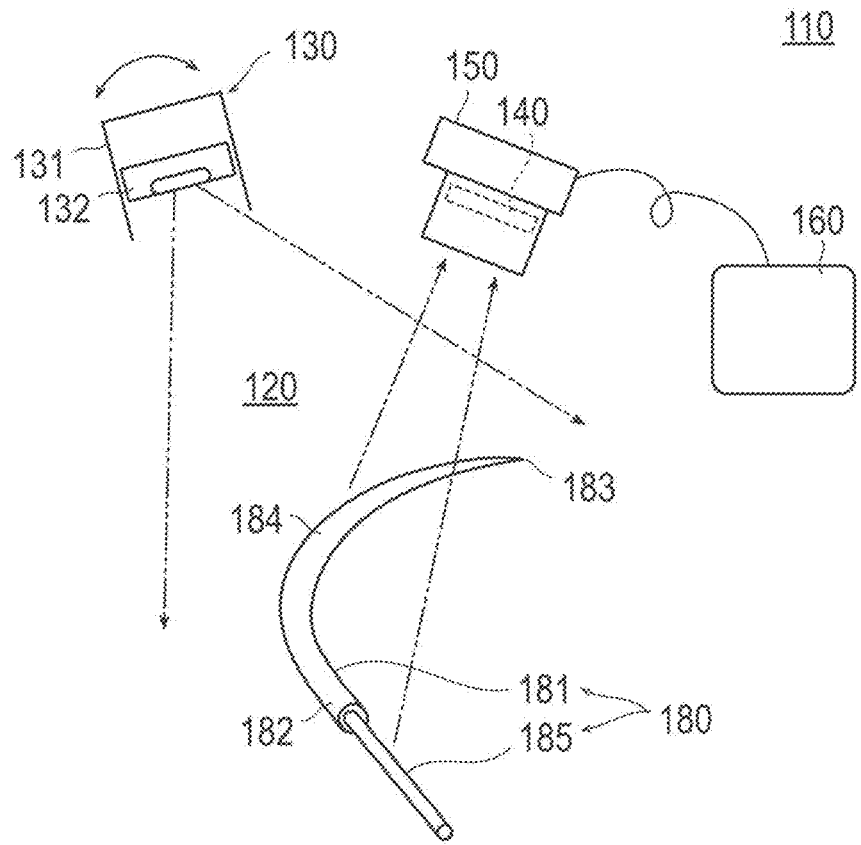
FIG. 8 is an explanatory drawing illustrating a medical product usage status checking apparatus according to a third embodiment.

FIG. 8 is an explanatory drawing illustrating a medical product usage status checking apparatus 110 according to a third embodiment.

Referring to FIG. 8, a medical product 180 emitting near-infrared fluorescence which is a target for checking existence or nonexistence thereof includes a luminescent agent emitting near-infrared fluorescence according to irradiation of excitation light on a surface thereof. As described in brief, the medical product usage status checking apparatus 110 according to the third embodiment is configured to include the medical product 180 emitting near-infrared fluorescence, an irradiation unit 130 which includes a light source 132 emitting excitation light which excites the luminescent agent and irradiates an operative field 120 where existence or nonexistence of the medical product 180 is to be checked with the excitation light emitted from the light source 132, an optical filter 140 which blocks the excitation light and transmits the near-infrared fluorescence emitted by the luminescent agent, a camera 150 (corresponding to an imaging unit) which receives the near-infrared fluorescence passing through the optical filter 140, and a monitor 160 (corresponding to a display unit) which displays an image captured by the camera 150. In the medical product usage status checking apparatus 110, in a case where the medical product 180 exists in the operative field 120, an image based on the near-infrared fluorescence of the medical product 180 is displayed on the monitor 160. Hereinafter, the description will be made in detail. In addition, the description of the contents common to the first embodiment will not be partially presented.

The medical product 180 illustrated in FIG. 8 is a light-emissive suture needle 181 where a luminescent agent is applied on a surface thereof and a suture thread 185 which is fixed to the suture needle 181. The suture thread 185 is formed with synthetic thread where the luminescent agent is kneaded in a resin material.

The suture needle 181 is configured to include a barrel portion 182 having a predetermined shape of cross section and a taper portion 184 of which size is decreased from the barrel portion 182 toward the sharp needle tip 183. A blind hole is formed in the base end portion of the barrel portion 182. As a base material for the suture needle 181, a stainless steel or the like is used. A luminescent agent is applied on the surface of the base material to form a thin-film light emitting layer, so that the light-emissive suture needle 181 is obtained. In addition, instead of the configuration that the entire suture needle 181 is allowed to emit light, the luminescent agent may be applied on a portion of the surface of the base material, so that only the portion of the suture needle 181 is configured to be allowed to emit light.

The suture thread 185 is made of a synthetic thread of nylon, polydioxanone, a polyglycolic acid, or the like where a luminescent agent is kneaded in a resin material. The suture thread 185 may be a woven thread or a mono filament. The suture thread 185 is configured so that the distal end thereof is inserted into the blind hole of the suture needle 181. By caulking the base end portion of the barrel portion 182, the suture thread 185 is fixed to the base end portion of the suture needle 181.

Similarly to the first embodiment, the luminescent agent is a medicine which can be used for a human body or an animal. An appropriate material may be used as long as the material emits the near-infrared fluorescence according to irradiation of the excitation light. Herein, the excitation wavelength is in a wavelength range suitable for allowing the luminescent agent to emit light. The excitation wavelength is preferably in a wavelength range of near-infrared light, and the light having a wavelength range of 600 nm to 1400 nm may be used. The near-infrared light has high transmittance with respect to human tissues such as skin, fat, and muscle and is capable of being transmitted down to about 5 mm to 20 mm under the surface of the tissue of the living body. Therefore, even in a case where the light-emissive medical product 180 exists in the living body, by allowing the excitation light to be transmitted down to the position, the medical product 180 can be allowed to emit light.

More specifically, similarly to the first embodiment, as the luminescent agent, indocyanine green (ICG) or an azo-boron complex compound disclosed in Japanese Patent Application No. 2010-23479 (JP 2011-162445 A) filed by the inventors of the present invention which emits near-infrared fluorescence according to irradiation of the excitation light may be used.

The irradiation unit 130 is configured to include a chassis 131 and a light source 132 which is arranged inside the chassis 131 to emit excitation light which excites the luminescent agent. The chassis 131 is configured with a metal material such as aluminum which does not transmit the excitation light. An operative field 120 where the existence or nonexistence of the medical product 180 is to be checked is irradiated with the excitation light emitted from the light source 132. The operative field 120 includes all the sites where the medical product 180 may exist, such as a bed in a surgical room and a surface of a floor as well as the living body. As the light source 132, for example, an LED or the like which emits the near-infrared excitation light having a wavelength range of 600 nm to 1400 nm may be used.

The optical filter 140, the camera 150, and the monitor 160 have the same configurations as the optical filter 40, the camera 50, and the monitor 60 of the first embodiment.

The camera 150 can image the suture needle 181 and the suture thread 185 by receiving the near-infrared fluorescence emitted by the luminescent agent of the suture needle 181 and the luminescent agent of the suture thread 185 by using a light-receiving element. Even in a case where the suture needle 181 and the suture thread 185 exist in the living body, the near-infrared fluorescence emitted by the luminescent agent of the suture needle 181 and the luminescent agent of the suture thread 185 passes through a living tissue, and the camera 150 images the suture needle 181 and the suture thread 185 by receiving the near-infrared fluorescence. In addition, at the same time, the camera 160 images the outline or the like of the human body.

In addition, the image captured by the camera 150 may be a monochrome image or may be a color image. The camera 150 may be configured so that the light source 132 is arranged in a ring shape around the lens. Accordingly, it is possible to more appropriately image the operative field 120.

The monitor is not particularly limited as long as the monitor 160 can display an image captured by the camera 150. The monitor may be a table-top display or may be a head-mounted display. The displayed image may be any one of a monochrome image and a color image. In a case where the suture needle 181 and the suture thread 185 exist in the operative field 120, the image based on the near-infrared fluorescence of the suture needle 181 and the near-infrared fluorescence of the suture thread 185 is displayed on the monitor 160. A user views the image displayed on the monitor 160 to check the existence or nonexistence of the suture needle 181 and the suture thread 185. If the image based on the near-infrared fluorescence appears, the user checks the existence of the suture needle 181 and the suture thread 185 in the operative field 120 and the positions where the suture needle 181 and the suture thread 185 exist.

Next, the functions of the embodiment will be described.

As illustrated in FIG. 8, the suture needle 181 to which the suture thread 185 is fixed exists in the operative field 120.

At the time of checking whether the medical product 180 exists in the operative field 120, the operative field 120 is irradiated with the near-infrared excitation light emitted from the light source 132 by the irradiation unit 130. At this time, the user widely scans the operative field 120 by moving the irradiation unit 130. During the scanning, if the suture needle 181 and the suture thread 185 are irradiated with the near-infrared excitation light, the luminescent agent on the surfaces of the suture needle 181 and the suture thread 185 is excited to emit the near-infrared fluorescence. In the case of using indocyanine green as the luminescent agent, the luminescent agent absorbs the near-infrared excitation light having a wavelength range of about 800 nm to be excited and emits the near-infrared fluorescence having a wavelength of about 850 nm.

The near-infrared fluorescence emitted by the suture needle 181 and the suture thread 185 passes through the optical filter 140 and is received by the camera 150, and thus, the image based on the near-infrared fluorescence of the suture needle 181 and the suture thread 185 is displayed on the monitor 160. In addition, reflection light reflected on a surface of the living body is received also by the camera 150, so that an image of the outline of the living body together with the suture needle 181 and the suture thread 185 is also displayed on the monitor 160. Since the image based on the near-infrared fluorescence appears on the monitor 160, the user can accurately and easily check the existence of the suture needle 181 and the suture thread 185 in the operative field 120 and the positions where the suture needle 181 and the suture thread 185 exist.

In the medical product usage status checking apparatus 110, since X-ray is not used to check the existence or nonexistence of the medical product 180, the problem in that operators and patients are exposed to the X-ray does not occur fundamentally. Furthermore even in the case of the medical product 180 made from a resin or a rubber which transmits the X-ray, it is possible to check the existence or nonexistence of the medical product.

As described above, in the third embodiment the medical product 180 emitting near-infrared fluorescence is a light-emissive medical product which includes the luminescent agent emitting the near-infrared fluorescence according to irradiation of the excitation light on the surface thereof. The medical product is the light-emissive suture needle 181 where the luminescent agent is applied on the surface thereof and the light-emissive suture thread 185 which is configured with a synthetic thread where the luminescent agent is kneaded in a resin material. Therefore, by applying the medical product usage status checking apparatus 110 according to the first embodiment, it is possible to check the existence or nonexistence of the suture needle 181 and the suture thread 185. If the image based on the near-infrared fluorescence appears on the monitor 160, the user can accurately and easily check the existence of the suture needle 181 and the suture thread 185 in the operative field 120 and the positions where the suture needle 181 and the suture thread 185 exist, so that it is possible to perform appropriate measures according to the usage status of the medical product such as removal of the suture needle 181 and the suture thread 185.

In the medical product usage status checking apparatus 110 according to the first embodiment, in a case where the suture needle 181 and the suture thread 185 exist in the operative field 120, the image based on the near-infrared fluorescence of the suture needle 181 and the suture thread 185 is displayed on the monitor 160. Therefore, it is possible to accurately and easily check the existence of the suture needle 181 and the suture thread 185 in the operative field 120 and the positions where the suture needle 181 and the suture thread 185 exist, so that it is possible to perform appropriate measures according to the usage status of the medical product such as removal of the suture needle 181 and the suture thread 185. In addition, since the existence or nonexistence is checked based on the near-infrared fluorescence, the present invention is not limited to the size of the medical product 180 which is a target for checking the existence or nonexistence thereof.

Fourth Embodiment

Figure 9:
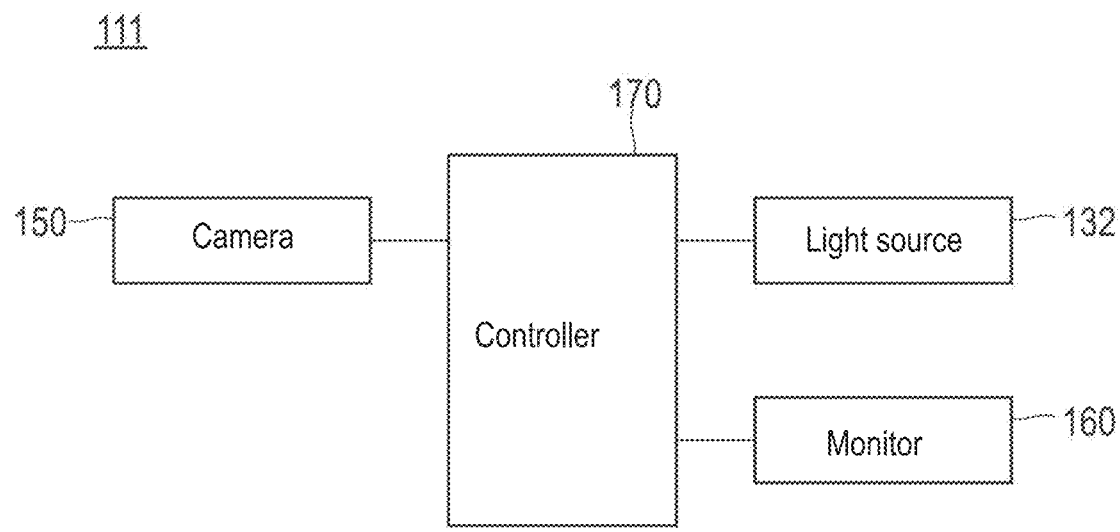
FIG. 9 is a schematic block diagram illustrating a configuration of medical product usage status checking apparatus according to a fourth embodiment.

FIG. 9 is a schematic block diagram illustrating a configuration of a medical product usage status checking apparatus 111 according to a fourth embodiment. The same components as the third embodiment are denoted by the same reference numerals, and the description thereof is not partially presented.

Similarly to the third embodiment, the medical product usage status checking apparatus 111 according to the fourth embodiment is configured to include a suture needle 181 and a suture thread 185 which emit near-infrared fluorescence, an irradiation unit 130, an optical filter 140, a camera 150, and a monitor 160. In a case where the suture needle 181 and the suture thread 185 exist in an operative field 120, an image based on the near-infrared fluorescence of the suture needle 181 and the suture thread 185 is displayed on the monitor 160.

In addition, in the fourth embodiment, the medical product usage status checking apparatus 111 includes a controller 170 (corresponding to a control unit) which informs that the suture needle 181 and the suture thread 185 exist in the operative field 120 in a case where the image based on the near-infrared fluorescence is detected.

The controller 170 performs image processes and image analysis on image data based on the near-infrared fluorescence to extract a light-emitting region, and when no light-emitting region is extracted, the controller determines that the suture needle 181 and the suture thread 185 do not exist in the operative field 120. On the other hand, when the light-emitting region is extracted, the controller 170 determines that the suture needle 181 and the suture thread 185 exist in the operative field 120. Therefore, the controller 170 informs the user that damage occurs in the suture needle 181 and the suture thread 185 in the operative field 120. The informing is performed by displaying on the monitor 160 or generating warning sound.

In the medical product usage status checking apparatus 111 according to the fourth embodiment, since the medical product usage status checking apparatus includes the controller 170 which informs that the suture needle 181 and the suture thread 185 exist in the operative field 120 in a case where the image based on the near-infrared fluorescence is detected, it is possible to accurately and easily check the existence of the suture needle 181 and the suture thread 185 in the operative field 120 and the positions where the suture needle 181 and the suture thread 185 exist, so that it is possible to more speedily perform appropriate measures according to the usage status of the medical product such as removal of the suture needle 181 and the suture thread 185.

(Modified Example of Medical Product 180)

As the form of the medical product 180 emitting near-infrared fluorescence, a form where the light-emissive suture needle 181 and a general non-emissive suture thread are connected in advance and a form where a general non-emissive suture needle and the light-emissive suture thread 185 are connected in advance may be used. In addition, a form where the light-emissive suture needle 181 and the light-emissive suture thread 185 are separated from each other may be used.

Figure 10:
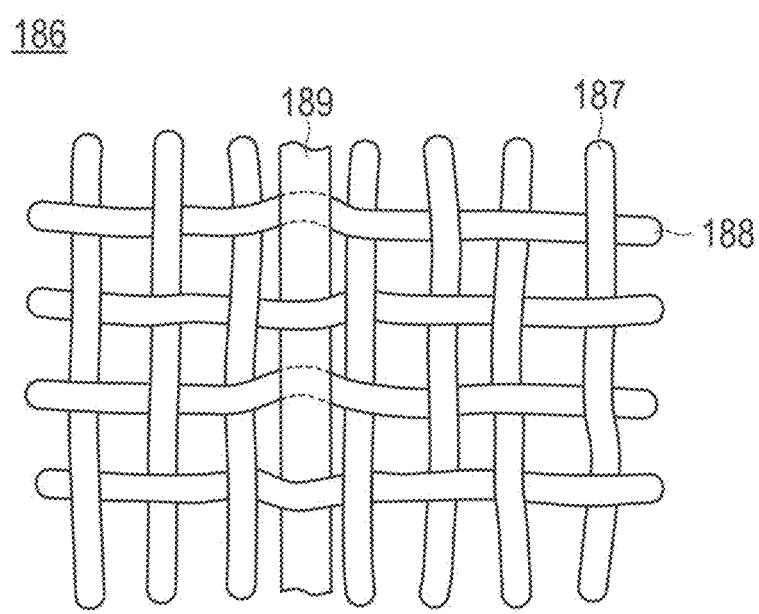
FIG. 10 is a drawing illustrating a cloth-formed consumable item as a medical product.

In addition, the medical product 180 is not limited to the suture needle 181 or the suture thread 185, but the present invention may be applied to a medical product 180 illustrated in, for example, FIG. 10.

The medical product 180 illustrated in FIG. 10 is a light-emissive cloth-formed consumable item 186 into which a synthetic thread 189 where the luminescent agent is kneaded in a resin material is woven. The cloth-formed consumable item 188 is, for example, a medical gauze 186. The gauze 186 illustrated is configured by plain-weaving plural warp yarns 187 and plural weft yarns 188 as composite yarns so as to alternately intersect each other with a substantially equal interval. The synthetic thread 189 where the luminescent agent is kneaded in a resin material as one of composite yarns is woven into the gauze 186. As the resin material of the synthetic thread 189, a thermoplastic resin such as a silicon-based resin, a polyvinyl chloride resin, a polypropylene resin, a polyester resin, and a polyethylene resin may be used. In addition, although only one line of the synthetic thread 189 is illustrated, plural lines of the synthetic thread 189 may be woven. A weaving form is not limited to the plain weaving, but a form of twill may be used.

Therefore, by applying the above-described medical product usage status checking apparatuses 110 and 111, it is possible to check the existence or nonexistence of the gauze 186. When the synthetic thread 189 emits light and the image based on the near-infrared fluorescence appears on the monitor 160, the user can accurately and easily check the existence of the gauze 186 in the operative field 120 and the position where the gauze 186 exists, so that it is possible to perform appropriate measures according to the usage status of the medical product such as removal of the gauze 186. Particularly, if the cloth-formed consumable item such as the gauze 186 absorbs blood, since it is difficult to visually check the cloth-formed consumable item, the medical product usage status checking apparatuses 110 and 111 are usefully applied.

Besides the cloth-formed consumable item. 186, the medical product 180 may be a light-emissive nonwoven cloth-formed consumable item which includes the above-described synthetic thread 189 without weaving. The nonwoven cloth-formed consumable item is, for example, a medical absorbent cotton. The absorbent cotton include one line or plural lines of the synthetic thread 189 where the luminescent agent is kneaded in a resin material without weaving.

Therefore, by applying the above-described medical product usage status checking apparatuses 110 and 111, it is possible to check the existence or nonexistence of the absorbent cotton. When the synthetic thread 189 emits light and the image based on the near-infrared fluorescence appears on the monitor 160, the user can accurately and easily check the existence of the absorbent cotton in the operative field 120 and the position where the absorbent cotton exists, so that it is possible to perform appropriate measures according to the usage status of the medical product such as removal of the absorbent cotton. Particularly, if the nonwoven cloth-formed consumable item such as the absorbent cotton absorbs blood, since it is difficult to visually check the cloth-formed consumable item, the medical product usage status checking apparatuses 110 and 111 are usefully applied.

Although the consumable item including at least one synthetic thread 189 is described as the cloth-formed consumable item 186 or the nonwoven cloth-formed consumable item, the cloth-formed consumable item 186 or the nonwoven cloth-formed consumable item may be formed by using only the synthetic thread 189 where the luminescent agent is kneaded in a resin material.

In addition, the present invention is not limited to the above-described medical product 180 (181, 185, and 186), but the present invention may be widely applied to a medical product 180 which has a risk of remaining in the operative field 120 and of which existence or nonexistence is desired to be checked. The medical product 180 may be a light-emissive medical product which includes the luminescent agent emitting the near-infrared fluorescence according to irradiation of excitation light on a surface thereof. Therefore, by applying the luminescent agent on various medical products such as scissors, pincettes, catheters, injection needles, and tubes or by configuring these medical products with a material in which the luminescent agent is kneaded, it is possible to check the existence or nonexistence of these medical products as the usage status of the medical products.

This patent application is based on Japanese Patent Application No. 2012-125710 filed on Jun. 1, 2012 and Japanese Patent Application No. 2012-125712 filed on Jun. 1, 2012, and the entire disclosure of which is hereby incorporated by reference herein.

REFERENCE SIGNS LIST

10, 11: Medical product usage status checking apparatus
20: Skin
21: Blood vessel
30: Irradiation unit
32: Light source
40: Optical filter
50: Camera (imaging unit)
60: Monitor (display unit)
70: Controller (control unit)
80: Medical product emitting near-infrared fluorescence
81: Subcutaneous implanted port (medical product)
82: Housing
83: Septum (constituent member)
83a: Core (separate piece)
84: Catheter
85: Sealed container (medical product)
86: Septum (constituent member)
86a: Core (separate piece)
87: Indwelling needle (medical product)
88: Hard inner needle
89: Soft outer needle (constituent member)
89a: Separate piece
90, 91: Needle
110, 111: Medical product usage status checking apparatus
120: Operative field
130: Irradiation unit
132: Light source
140: Optical filter
150: Camera (imaging unit)
160: Monitor (display unit)
170: Controller (control unit)
180: Medical product emitting near-infrared fluorescence
181: Suture needle (medical product)
185: Suture thread (medical product)
186: Gauze, cloth-formed consumable item (medical product)
189: Synthetic thread where the luminescent agent is kneaded in a resin material

The invention claimed is:
1. A medical product usage status checking apparatus comprising:
a medical product, the medical product comprising at least one integral light-emissive constituent member, which at least one integral light-emissive constituent member includes an area upon which a luminescent agent exists, the luminescent agent emitting near-infrared fluorescence according to irradiation of an excitation light on the area;
an irradiation unit which includes a light source emitting irradiation of the excitation light, which excitation light excites the luminescent agent, and which irradiation unit irradiates the area of the at least one integral light-emissive constituent member, or any damaged portions thereof, with the excitation light emitted from the light source;

an optical filter which blocks the excitation light and transmits the near-infrared fluorescence emitted by the luminescent agent;

an imaging unit which receives the near-infrared fluorescence passing through the optical filter;

a display unit which displays an image captured by the imaging unit; and a control unit which is connected to the light source, the imaging unit and the display unit, wherein the control unit determines and informs that damage had occurred to the area of the at least one integral light-emissive constituent member, where the at least one integral light-emissive constituent member, including a surface of predetermined light-emitting area, has now taken the form of a separate first light-emitting portion of the area and a separate second light-emitting portion of the area, as detected by the control unit, wherein the control unit calculates the area of the separate first light-emitting portion based on the near-infrared fluorescence of the separate first light-emitting portion and the control unit calculates the area of the separate second light-emitting portion based on the near-infrared fluorescence of the separate second light-emitting portion and determines that when area of the separate second light-emitting portion as compared to the area of the separate first light-emitting portion reaches a pre-determined threshold, the control unit informs that damage has occurred to the at least one integral light-emissive member.

2. The medical product usage status checking apparatus according to claim 1, wherein the at least one integral light-emissive constituent member is one selected from the group consisting of a septum which is used for a subcutaneous implanted port, a septum which is used for a sealed container and into which a needle is inserted, and a soft outer needle into which a hard inner needle of an indwelling needle is inserted.

3. The medical product usage status checking apparatus according to claim 1, wherein the at least one integral light-emissive constituent member is configured so that the luminescent agent is applied on a surface thereof or is formed with a material in which the luminescent agent is kneaded.

4. The medical product usage status checking apparatus according to claim 2, wherein the at least one integral light-emissive constituent member is configured so that the luminescent agent is applied on a surface thereof or is formed with a material in which the luminescent agent is kneaded.

* * * * *